Figure 1:
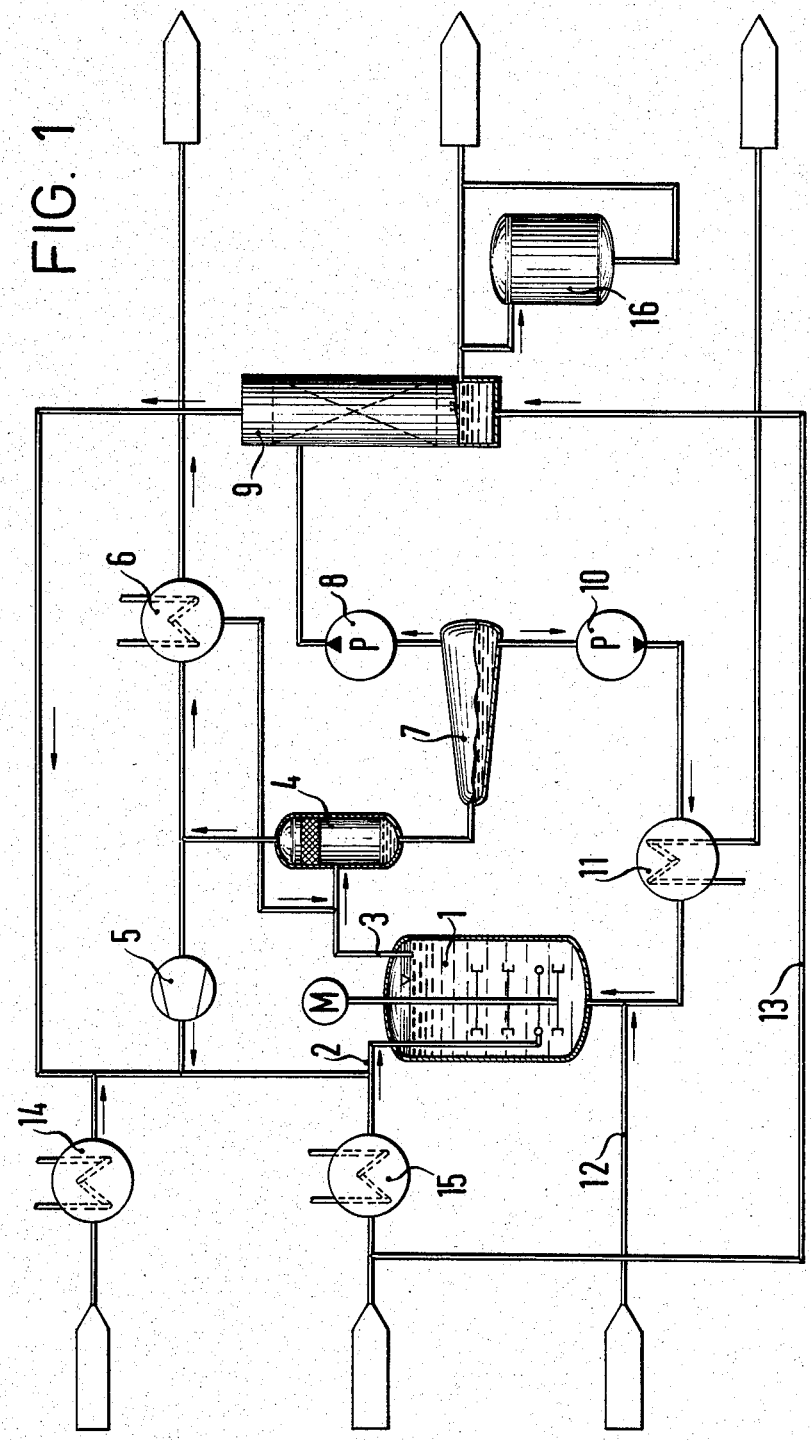

United States Patent [19]

Cornils et al.

[11] Patent Number: 4,523,036
[45] Date of Patent: Jun. 11, 1985

[54] PROCESS FOR THE PREPARATION OF ALDEHYDES

[75] Inventors: Boy Cornils, Dinslaken; Josef Hibbel, Oberhausen; Bernhard Lieder, Bottrop; Joachim Much, Oberhausen; Volkmar Schmidt, Oberhausen; Ernst Wiebus, Oberhausen; Werner Konkol, Oberhausen, all of Fed. Rep. of Germany

[73] Assignee: Ruhrchemie Aktiengesellschaft, Fed. Rep. of Germany

[21] Appl. No.: 533,645

[22] Filed: Sep. 16, 1983

[30] Foreign Application Priority Data

Sep. 18, 1982 [DE] Fed. Rep. of Germany ....... 3234701

[51] Int. Cl.³ .............................................. C07C 45/50
[52] U.S. Cl. ...................................... 568/454; 568/909
[58] Field of Search ........................ 568/454, 909, 883

[56] References Cited

U.S. PATENT DOCUMENTS 3,939,385  5/1976  Nienburg et al. ................... 568/454
4,248,802  2/1981  Kuntz ................................... 568/454
4,258,215  3/1981  Dawes .................................. 568/454

Primary Examiner—Werren B. Lone
Attorney, Agent, or Firm—Jordan B. Bierman

[57] ABSTRACT

The continuous preparation of aldehydes from olefins and synthesis gas by the use of a water-soluble catalyst system containing rhodium. The reaction takes place at 100 to 30,000 kPa and 90° to 150° C. The proportion of gaseous components in the liquids is 5 to 30% by volume, based on the total gaseous and liquid components, the volume ratio of aqueous to organic parts being 1:1 to 100:1. After completion of the reaction, the liquid components and the gaseous components are separated into a liquid phase and a gaseous phase, then the liquid phase is divided into aqueous and organic parts, separation taking place without previous cooling. The heat contained in the reaction product is either removed by water or steam, or is carried over to the hydroformylation products.

42 Claims, 2 Drawing Figures

PROCESS FOR THE PREPARATION OF ALDEHYDES

This Application claims the priority of German Application No. 32 34 701.4, filed Sept. 18, 1982.

The present invention relates to a process for the preparation of aldehydes by the hydroformylation of olefins in the presence of water-soluble rhodium complex catalysts.

It is known to prepare aldehydes, and alcohols as well, by the reaction of olefins with synthesis gas; i.e. a mixture of carbon monoxide and hydrogen. The reaction is catalyzed by hydridometal carbonyls, preferably those containing metals of Group VIII of the Periodic Table. Cobalt is widely used in industry as a catalyst metal, but rhodium is gaining in importance. In contrast to cobalt, rhodium allows the reaction to be carried out at low pressure; moreover, n-aldehydes are principally formed and iso-aldehydes are produced only to a lesser degree. Finally, hydrogenation of the olefins to undesired saturated hydrocarbons is appreciably less with the use of rhodium catalysts than with cobalt catalysts.

In the processes known to industry, the rhodium catalyst is used in the form of hydridorhodium carbonyls containing additional ligands. Tertiary phosphines or phosphites have proved especially suitable as ligands. Through their use, the reaction pressure can be reduced to less than 30,000 kPa.

In this process, the separation of the reaction products from the homogeneously dissolved catalysts has proved to be unsatisfactory. In general, it is necessary to distill the reaction products out of the reaction mixture. In practice, however, this method can only be adopted for the hydroformylation of lower olefins up to about pentene. Moreover, it has been shown that the associated thermal load leads to appreciable catalyst losses due to the decomposition of the rhodium complexes.

These shortcomings are avoided by the use of catalyst systems which are soluble in water. Such catalysts are described, for example, in German Pat. No. 26 27 354. The solubility of the rhodium complex compounds is achieved in this case by the use of trisulfonated triaryl phosphines as complex components. The separation of the catalyst from the reaction product after the hydroformylation takes place simply by the separation of the aqueous phase and the organic phase; i.e. without additional thermal loading of the reaction mixture being necessary for distillation of the reaction products. However, the teaching of the above-mentioned German Patent is limited to a discontinuous process in autoclaves, which is not suitable for industrial application. According to another process, solubility of the catalyst system in water is achieved by the use of singly or multiply carboxylated aryl phosphine ligands.

It is an object of the present invention to provide a process for preparing aldehydes of the above-mentioned type, which can be carried out on a continuous basis, without unduly damaging the catalyst used.

The invention consists of a continuous process for preparing aldehydes by the reaction of olefins with carbon monoxide and hydrogen in the presence of water and water-soluble rhodium phosphine complex compounds. The reaction takes place at elevated temperatures and pressures of 100 to 30,000 kPa. The reactants are homogeneously mixed and caused to react at temperatures of 90° C. to 150° C. and the proportion of gaseous components in the liquid components is adjusted to 5% to 30% by volume, based on the total gaseous and liquid components, the volume ratio of the aqueous part to the organic part of the liquid being 1:1 to 100:1, and the liquid and gaseous components are separated, then the liquid components are divided into aqueous and organic parts, in each case without previous cooling, and the heat of reaction is removed.

The new process not only insures that the catalyst system is separated under mild conditions and reused, but also enables the reaction to be carried out under technically and economically optimum conditions. The fact that the process according to the invention permits the heat of reaction to be easily recovered without adversely affecting the life of the catalyst is of particular importance.

According to known methods, the heat of reaction can be removed by means of water or steam. It has proved particularly useful, in the present invention, to carry over the heat of reaction directly to the products of the hydrofromylation, without the use of an auxiliary medium. This permits vaporization and purification of such products by distillation using the heat of reaction.

The process according to the invention is particularly suitable for the conversion of olefins with 2 to 15 carbon atoms to aldehydes or alcohols with one additional carbon atom. The reactants, i.e. olefin and synthesis gas, are fed into the reactor either together or separately. It is advisable to preheat the reactants, preferably to the temperature at which the reaction takes place. It has proved useful to employ process waste heat for preheating, e.g. the heat which can be recovered during condensation of the reaction products in the course of purification by distillation.

The reaction of the starting materials takes place at temperatures of 90° to 150° C. Due to the absence of an additional thermal load for the removal of reactants by distillation, the catalyst is only very slightly deactivated in continuous operation. The slight damage to the catalyst which occurs is well within economically acceptable limits.

The reaction takes place in a system consisting of a liquid and a gaseous components. The liquid phase comprises two components which are either insoluble or only very slightly soluble in each other; the aqueous catalyst solution, the gaseous or liquid olefin (whether the olefin is gaseous or liquid depends on its molecular size and/or the reaction conditions chosen) and the liquid organic reaction product, and optionally another solvent, are present. It is essential that the aqueous portion be saturated with the gaseous reactants. In order to achieve this, it is necessary to ensure as large a contact surface as possible between the liquid—that is to say the aqueous and organic components—and the gaseous portion so that the proportion of gaseous components in the liquid is adjusted to 5 to 30% by volume, based on the total of the gases and liquids.

This objective can be realized by various means. According to one version of the invention, the gaseous starting materials, i.e. olefin and synthesis gas, are introduced into the reactor which contains the remaining starting materials under vigorous agitation. According to another variation, the gaseous reaction partners are fed into the liquid reactor contents through appropriate distribution devices. Screens or frits are, for example, suitable. It is also possible to combine stirring and distribution of gaseous reactants by, for example, the use of a gas stirrer.

A very important aspect of the present invention is to maintain the proportion of the organic part in the reaction mixture small, for, surprisingly enough, the organic phase does not assist the solubility of the reactants in the aqueous phase. In this way it is possible to prevent the reaction product from entering into undesirable side reactions which cannot be excluded if the residence time of the product in the reactor increases.

Thus, the volume ratio of the aqueous part to the organic part according to the invention is 1:1 to 100:1, preferably 10:1 to 100:1. Various methods of regulating the above-mentioned volume ratio present themselves. According to one form of the new procedure, a portion of the reaction mixture is removed from the reactor and subjected to phase separation so that the desired volume ratio in the reactor is achieved after the recycling of the aqueous phase. According to another version of the invention, the phase separation can also be carried out in a stabilizing zone within the reactor.

In the new process, the phase separation described above takes place without previous cooling of the reaction mixture. Thus, the gaseous olefins are dissolved only in small quantities in the components of the reaction mixture, which are liquid under the given circumstances, and are carried away with the reaction product.

The synthesis gas used for hydroformylation contains carbon monoxide and hydrogen, preferably in a volume ratio of 1:1. However, it is possible to vary this ratio to achieve special effects; e.g. to increase the rate of reaction.

As catalysts, complex rhodium compounds are used which, apart from the carbon monoxide and hydrogen, also contain carboxylated or sulfonated phosphines. Such phosphines are derived most desirably from triaryl phosphines, and phenyl and naphthyl are preferred as the aryl groups. It is not necessary for all three aryls to carry sulfonic acid or carboxylic groups. It has been shown that even one sulfonic acid group or carboxylic group in the phosphine molecule of the complex provides sufficient water solubility. The catalyst can be added performed to the reaction mixture, but it is also possible to form it in situ. Normally, rhodium is added in the amount of 50 to 800 ppm, based on the aqueous catalyst solution. The sulfonated or carboxylated triaryl phosphine must be in excess, based on the rhodium complex. It has proved particularly effective to add 10 to 100 g molecules of sulfonated or carboxylated phosphine per gram-atom of rhodium. The reaction pressures are in the range of 100 to 30,000 kPa.

Figure 2:
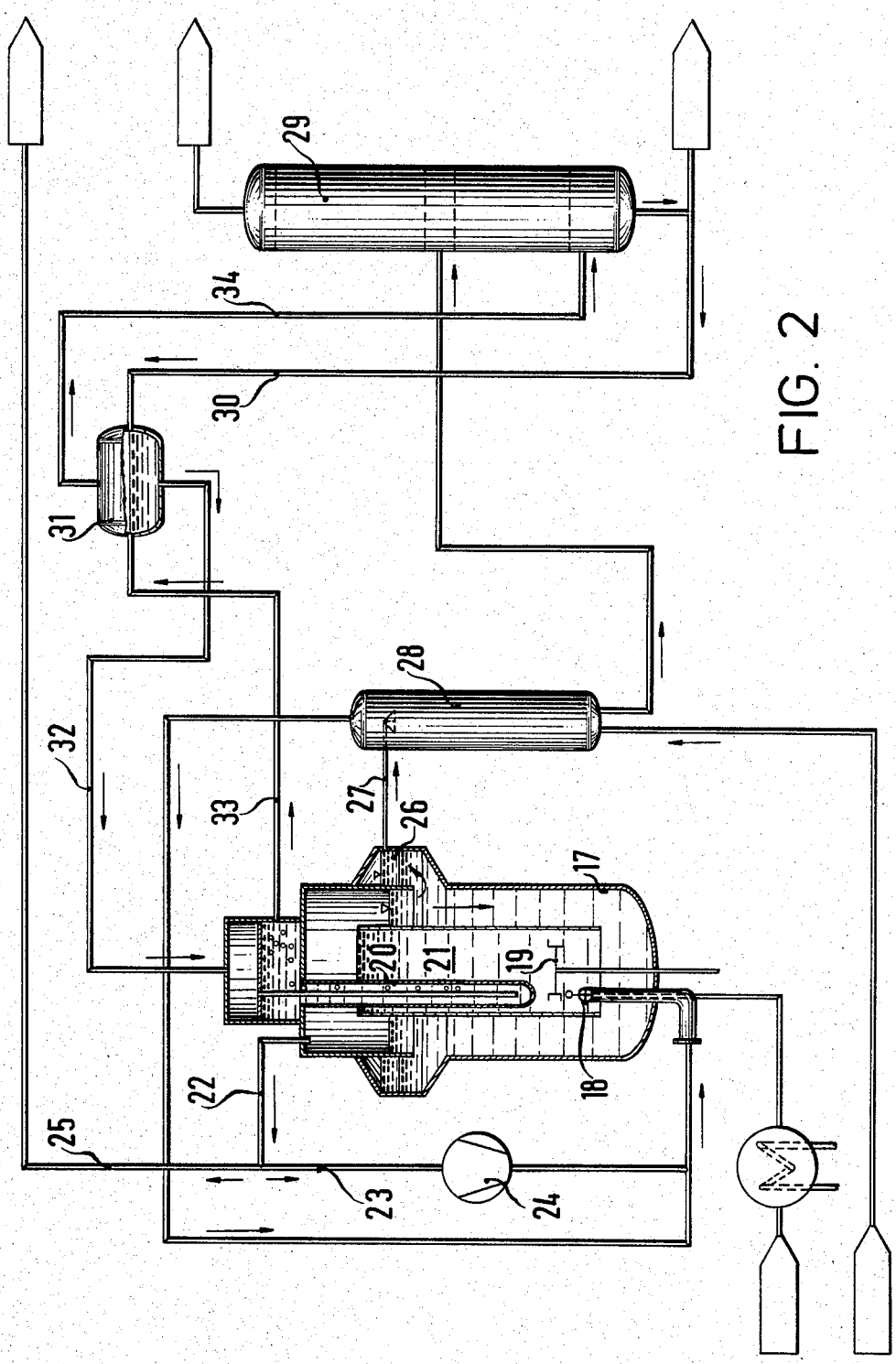

In the accompanying drawing, constituting a part hereof, and in which like reference characters indicate like parts, FIG. 1 is a flow diagram of one form of the invention; and FIG. 2 is a flow diagram of a modified form of the invention which is particularly suitable for use on a commercial scale.

In FIG. 1, the catalyst system dissolved in water is present in reactor 1. Olefin and synthesis gas are preheated and fed into reactor 1 through lines 2 and the reaction is commenced unter vigorous agitation. The reaction product mixed with aqueous catalyst solution, unreacted synthesis gas and olefin leaves reactor 1 through dip pipe 3. The gaseous components—mainly synthesis gas, olefin and in some cases saturated hydrocarbon formed from the olefin—are separated from the liquid products in separating vessel 4 and recycled to the reactor through circulatory compressor 5. Part of the cycle gas is freed from the condensable reaction products in cooler 6 and released into the waste gas system. The hot liquid from separating vessel 4 is fed into phase separator 7 without prior cooling. Here the raw organic reaction product separates very easily from the aqueous catalyst phase. Dispensing with the cooling of the organic phase before separation of the unreacted reactants considerably facilitates the necessary recirculation of the gaseous olefins through a stripping column 9. They are much less soluble in the hot organic reaction product (the raw aldehyde) than in the cooled reaction product.

While the organic reaction product is fed into stripping column 9 by means of pump 8, pump 10 returns the aqueous catalyst to reactor 1, whereby the heat of the exothermic reaction is released in heat exchanger 11, process steam being produced. With the cooled catalyst, water is fed into the reactor through line 12 to compensate for the loss of water through the waste gas and the raw Oxo product. The hot raw Oxo product flows towards the stripping column 9 countercurrent to a portion of the synthesis gas which is flowing towards the column through line 13. In this way, the synthesis gas is charged with the olefin dissolved in the Oxo raw product and is then fed into reactor 1 at elevated temperature. A further portion of the synthesis gas is preheated with process heat in heat exchanger 15. Before being fed into the reactor, the fresh olefin is also preheated and vaporized in heat exchanger 14 with waste heat from the aldehyde distillation, while the Oxo raw product from stripping column 9 is fed uncooled directly to a distillation device (not shown). Buffer vessel 16 serves as an interim product storage facility in case of breakdown.

In FIG. 2, the aqueous catalyst solution is present in reactor 17. The synthesis gas and olefin are fed in through twin nozzles 18 which act as preliminary distributors; gas stirrer 19 serves to finely distribute the reactants. The heat from the exothermic reaction is removed through cooling register 20. The liquid and gaseous components rise in guide pipe 21 of the reactor, and separate at the upper end thereof. The gaseous components are either recycled to the reactor via line 23 and circulatory gas compressor 24, or are carried off as waste gas through line 25. The aqueous catalyst solution separates from the organic product formed in annular separator 26. Through line 27, the raw product is fed into stripping column 28 and is there freed from dissolved olefin by the synthesis gas in countercurrent flow. The olefin-free raw product is separated into the n- and iso-components in column 29. The heat necessary for the distillation is taken directly from cooling register 20 by liquid aldehyde fed from the bottom of column 29 through line 30, phase separator 31, and line 32 into the cooling register, vaporized there and refed as gaseous aldehyde to column 29 through line 33, phase separator 31 and line 34.

EXAMPLE 1 (COMPARISON)

In a reactor at 125° C. under 5,000 kPa pressure, 50 liters of a mixture of aqueous catalyst solution, Oxo raw product, synthesis gas and propylene are maintained in a homogeneous phase by vigorous agitation. The continuously drawn off product stream containing catalyst solution, Oxo raw product, excess propylene and synthesis gas is cooled before product separation. Under the selected conditions about 4.5 kg propylene/kg of Oxo product are dissolved in the cooled Oxo raw product. The density of this organic phase is 0.6 g/cm$^3$. The production of propylene dissolved in the aqueous phase is negligible. The difference in density between the aqueous phase (density=1.15 g/cm$^3$) and the organic phase is 0.55 g/cm$^3$. Thus, the two phases separate quickly and completely from each other.

EXAMPLE 2

The reaction takes place under the same conditions as in Example 1. In contrast to Example 1, however, the drawn off product stream of catalyst solution, Oxo raw product, excess propylene, and synthesis gas is not cooled before the product separation, but kept at the reaction temperature. Only 0.4 kg propylene/kg of Oxo raw product remain dissolved in the Oxo raw product. This means that the average density of the organic phase of 0.75 g/cm$^3$ is higher than in Example 1, so the difference in density between and organic and aqueous phases is reduced to 0.4 g/cm$^3$.

Surprisingly, the phases separate from each other just as quickly and completely as in the previous example, despite the smaller difference in density. The ability to separate organic and aqueous phases without prior cooling in an economically satisfactory and technically simple manner considerably facilitates circulation control of the propylene. As a result, the amount of propylene to be separated through stripping column 9 and returned to reactor 1 is reduced from 4.5 to 0.4 kg/kg of Oxo raw product, which means an appreciable energy saving.

EXAMPLE 3

In a reactor 1, under the reaction conditions of Example 1, 50 liters of a mixture of aqueous catalyst solution, Oxo raw product, synthesis gas and propylene are maintained in a homogeneous phase by vigorous stirring. To achieve phase distribution between aqueous and organic phases and to remove the heat of reaction via circulatory pump 10, 100 liters of aqueous catalyst solution per hour are circulated. Under the selected reaction conditions, 10 liters of raw aldehyde per hour are formed from propylene, so that the ratio of aqueous to organic phase is 10:1.

The average residence time of the raw aldehyde in the reactor is 27 minutes. 0.5% by weight of undesired high-boiling by-products are contained in the Oxo raw product.

EXAMPLE 4

The reaction conditions are the same as in Example 1, but only 35 liters of catalyst solution per hour are circulated. Thus, the average residence time of the raw aldehyde in the reactor increases to 69 minutes. Under these conditions the Oxo raw product contains about 1.5% by weight of undesired, high-boiling by-products.

With a reactor having an internal cooling register and without catalyst circulation, the speed of the stirrer is selected so that the phase in the mixing zone of the reactor contains not more than 10% raw aldehyde homogeneously distributed. The level of the aldehyde floating on the aqueous catalyst solution in the damping zone is low due to suitable level control (which can be achieved e.g. by the selection of various outlets placed at different heights or by increasing the contents of the aqueous catalyst phase), thus enabling residence times of the raw aldehyde in the synthesis part to be maintained at 30 minutes or less.

It is surprising that the reduction in the rotational speed of the stirrer, which permits separation of the organic and aqueous phase in the upper section of the reactor, has no detrimental effect on its throughput capacity. It is evident that a sufficient saturation of the reactants in the aqueous catalyst phase is achieved in the vigorously agitated zone.

What we claim is:

1. In a process for the preparation of an aldehyde comprising contacting a starting material comprising an olefin, carbon monoxide, hydrogen and water in the presence of a water-soluble rhodium-phosphine complex as a catalyst, wherein a portion of said starting material, under the reaction conditions, forms a first gaseous component and a second portion of said starting material, under the reaction conditions, forms a first liquid component by homogeneously mixing said first component at a temperature of about 90° to about 150° C. and a pressure of about 100 to about 30,000 kPa whereby a product is formed, said product comprising second gaseous and second liquid components, and cooling said product, the improvement comprising the proportion of said first gaseous component in said first liquid component being about 5% to about 30% by volume, based on the total of said first gaseous and first liquid components, and separating said second liquid and said gaseous components from each other to form a liquid phase and a gaseous phase, said separating occurring prior to said cooling.

2. The process according to claim 1, wherein the reactants are preheated to said reaction temperature before said reaction.

3. The process according to claim 2 wherein preheating is carried out with process waste heat.

4. The process according to claim 1 wherein the gaseous components are introduced into said liquid components under vigorous agitation.

5. The process according to claim 1 wherein the gaseous components are introduced into the reactor by means of distribution devices.

6. The process according to claim 1 wherein said volume ratio is 10:1 to 100:1.

7. The process according to claim 1 wherein said separation of the liquid phase into aqueous and organic segments takes place in a damping zone.

8. The process of claim 2 wherein the first gaseous components are introduced into said first liquid components under vigorous agitation.

9. The process of claim 3 wherein the first gaseous components are introduced into said first liquid components under vigorous agitation.

10. The process according to claim 2 wherein the removal of the heat of reaction takes place without the aid of an auxiliary medium by vaporization of at least part of said reaction products.

11. The process according to claim 3 wherein the removal of the heat of reaction takes place without the aid of an auxiliary medium by vaporization of at least part of said reaction products.

12. The process according to claim 2 wherein said separation of the liquid phase into aqueous and organic segments takes place in a damping zone.

13. The process according to claim 3 wherein said separation of the liquid phase into aqueous and organic segments takes place in a damping zone.

14. The process according to claim 4 wherein said separation of the liquid phase into aqueous and organic segments takes place in a damping zone.

15. The process according to claim 5 wherein said separation of the liquid phase into aqueous and organic parts takes place in a damping zone.

16. The process according to claim 6 wherein said separation of the liquid phase into aqueous and organic parts takes place in a damping zone.

17. The process of claim 1 further comprising recycling said second gaseous component whereby said second gaseous component, upon said recycling, becomes a portion of said first gaseous component in the next succeeding contacting step.

18. The process of claim 1 further comprising removing the heat of reaction from at least one of said products.

19. The process of claim 1 further comprising at least one of (1) preheating at least one portion of said first component before said contacting step and (2) distilling said aldehyde, wherein said aqueous segment is recycled as a portion of said first component, said second gaseous component is recycled to form a portion of said first gaseous component in the next succeeding reacting step, and removing the heat of reaction from at least one portion of said product for use in at least one of preheating said first components and distilling said aldehyde.

20. The process of claim 1 wherein said olefin has 2-5 carbon atoms and said aldehyde has one carbon atom more than said olefin.

21. The process of claim 1 wherein said water soluble rhodium-phosphine complex comprises phosphines portions selected from sulfonated and carboxylated triaryl phosphines.

22. The process of claim 1 wherein said olefin has 2-15 carbon atoms, said aldehyde has one carbon atom more than said olefin, and said water soluble rhodium-phosphine complex comprises phosphine portions selected from sulfonated and carboxylated triaryl phosphine.

23. The process of claim 19 wherein said olefin has 2-15 carbon atoms, said aldehyde has one carbon atom more than said olefin, and said water soluble rhodium-phosphine complex comprises phosphine portions selected from sulfonated and carboxylated triaryl phosphine.

24. In a process for the preparation of an aldehyde comprising contacting a starting material comprising an olefin, carbon monoxide, hydrogen and water in the presence of a water-soluble rhodium-phosphine complex as a catalyst, wherein a portion of said starting material, under the reaction conditions, forms a first gaseous component and a second portion of said starting material, under the reaction conditions, forms a first liquid component by homogeneously mixing said first component at a temperature of about 90° to about 150° C. and a pressure of about 100 to about 30,000 kPa whereby a product is formed, the improvement which comprises the proportion of said first gaseous component in said first liquid component being from about 5% to about 30% by volume based on the total of said first components.

25. The process of claim 24 wherein said first liquid component comprises an aqueous part and an organic part.

26. The process of claim 25 wherein the ratio of said aqueous part to said organic part is from about 1:1 to about 100:1.

27. The process of claim 24 which further comprises removing the heat of reaction from at least one of said products.

28. The process of claim 24 wherein said olefin has 2-15 carbon atoms and said aldehyde has one carbon more than said olefin.

29. The process of claim 24 wherein said water soluble rhodium-phosphine complex comprises phosphine portions selected from sulfonated and carboxylated triaryl phosphines.

30. The process according to claim 27 wherein the removal of the heat of reaction takes place with the aid of an auxiliary medium.

31. The process according to claim 27 wherein the removal of the heat of reaction takes place without the aid of an auxiliary medium by vaporization of at least part of said reaction products.

32. The process of claim 30 wherein said medium is water or steam.

33. The process according to claim 30 wherein said separation of the liquid phase into aqueous and organic parts takes place in a damping zone.

34. In a process for the preparation of an aldehyde comprising contacting a starting material comprising an olefin, carbon monoxide, hydrogen and water in the presence of a water-soluble rhodium-phosphine complex as a catalyst, wherein a portion of said starting material, under the reaction conditions, forms a first gaseous component and a second portion of said starting material, under the reaction conditions, forms a first liquid component by homogeneously mixing said first component at a temperature of about 90° to about 150° C. and a pressure of about 100 to about 30,000 kPa whereby a product is formed, said product comprising second liquid and second gaseous components, and cooling said product, the improvement which comprises separating said second liquid and said second gaseous components from each other to result in a liquid phase and a gaseous phase, said separating occurring prior to said cooling of said product.

35. The process of claim 34 wherein said liquid phase comprises an organic segment and an aqueous segment and said segments are separated from each other prior to said cooling of said product.

36. The process of claim 25 further comprising recycling said aqueous segment as a portion of said first components.

37. The process of claim 34 further comprising recycling said second gaseous component whereby said second gaseous component, upon said recycling, becomes a portion of said first gaseous component in the next succeeding contacting step.

38. The process of claim 34 further comprising removing the heat of reaction from at least one of said products.

39. The process of claim 34 wherein said olefin has 2-15 carbon atoms and said aldehyde has one carbon atom more than said olefin.

40. The process of claim 34 wherein said water soluble rhodium-phosphine complex comprises phosphine portions selected from sulfonated and carboxylated triaryl phosphines.

41. The process of claim 26 wherein said olefin has 2-15 carbon atoms, said aldehyde has one carbon atom more than said olefin, and said water soluble rhodium-phosphine complex comprises phosphine portions selected from sulfonated and carboxylated triaryl phosphine.

42. The process of claim 35 wherein said olefin has 2-15 carbon atoms, said aldehyde has one carbon atom more than said olefin, and said water soluble rhodium-phosphine complex comprises phosphine portions selected from sulfonated and carboxylated triaryl phosphine.

* * * * *